United States Patent [19]

Takatori et al.

[11] 4,382,142
[45] May 3, 1983

[54] THIADIAZOLE DERIVATIVES AND PROCESS FOR PREPARING SAME

[75] Inventors: Kichitaro Takatori, Nagoya; Takashi Yamaguchi, Urawa; Masahiko Nagakura, Sayama, all of Japan

[73] Assignee: Kowa Co., Ltd., Nagoya, Japan

[21] Appl. No.: 203,152

[22] Filed: Nov. 3, 1980

[30] Foreign Application Priority Data

Oct. 18, 1978 [JP] Japan .................... 53-128146

[51] Int. Cl.³ ............ C07D 285/12; A61K 31/425
[52] U.S. Cl. ............................. 548/139; 424/270
[58] Field of Search ................... 548/139; 424/270

[56] References Cited

U.S. PATENT DOCUMENTS 4,092,148  5/1978  Cebalo .................... 548/139

Primary Examiner—Nicky Chan
Assistant Examiner—Frederick W. Pepper

Attorney, Agent, or Firm—Oblon, Fisher, Spivak, McClelland & Maier

[57] ABSTRACT

A compound represented by the formula,

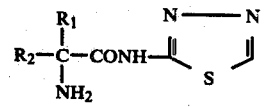

wherein $R_1$ represents a hydrogen atom, and $R_2$ represents a lower alkyl group, an aryl group, an aralkyl group, a lower alkylthio lower alkyl group, a lower alkyl group substituted by a carboxyl or hydroxyl group, or a 3-indolymethyl group, or wherein $R_1$ and $R_2$ define in combination an alkylene group, or a pharmaceutically acceptable acid addition salt thereof, is an anti-tumor agent for leukemia and malignant tumors.

3 Claims, No Drawings

THIADIAZOLE DERIVATIVES AND PROCESS FOR PREPARING SAME

BACKGROUND OF THE INVENTION

1. Field of the Invention

This invention relates to novel thiadiazole derivatives or acid addition salts thereof, and a process for producing the same.

2. Description of the Prior Art

There have heretofore been developed and used a number of anti-tumor agents for malignant tumors and leukemia. However, these anti-tumor agents are highly toxic and hence require especial care, for their actual application, in avoiding any adverse side effects. Another disadvantage is that when being formulated, such agents encounter much inconvenience due primarily to their relatively poor solubility in water or other media. Accordingly, the conventional anti-tumor agents are not necessarily satisfactory.

In order to overcome the above noted disadvantages of the prior art techniques, a variety of anti-tumor agents have been studied. In the studies leading to the present invention, it has been discovered that thiadiazole derivatives and acid addition salts thereof of a specific class can achieve the desired and satisfactory results.

SUMMARY OF THE INVENTION

One object of the present invention is to provide novel thiadiazole derivatives or acid addition salts thereof which are substantially devoid of the defects of the existing anti-tumor agents and which possess strong healing effects on leukemia and malignant tumors.

It is another object of the invention to provide a process for producing these novel thiadiazole derivatives or acid addition salts thereof.

Thes and other objects and advantages of the invention as hereinafter will become readily apparent can be attained by the discovery of compounds represented by the formula (I),

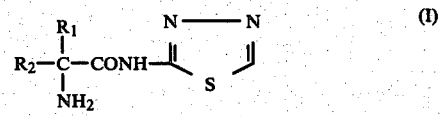

wherein $R_1$ represents a hydrogen atom, and $R_2$ represents a lower alkyl group, an aryl group, an aralkyl group, a lower alkylthio lower alkyl group, a lower alkyl group substituted by a carboxyl or hydroxyl group, or a 3-indolylmethyl group, or wherein $R_1$ and $R_2$ define in combination an alkylene group, and pharmaceutically acceptable acid addition salts thereof.

Such derivatives and acid addition salts have been found to have an extremely low degree of toxicity and exhibit excellent anti-tumor effects on leukemia and malignant tumors such as sarcoma, cancer and the like. Particularly, the acid addition salts are desirable because they are readily soluble in water.

These derivatives and acid addition salts can be administered by injection (intravenous, subcutaneous and intramuscular), an oral route and other routes.

DETAILED DESCRIPTION OF THE PREFERRED EMBODIMENTS

The compounds of the formula (I) according to the invention can be prepared, for example, by reacting 2-amino-1,3,4-thiadiazole of the formula (III) or a reactive derivative thereof with an amino acid of the formula (II) or a reactive derivative thereof, as illustrated by the following reaction scheme:

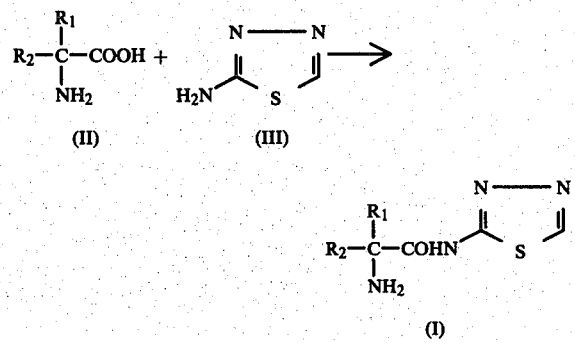

wherein $R_1$ and $R_2$ have the same meanings as defined hereinbefore.

One starting compound or 2-amino-1,3,4-thiadiazole of the formula (III) useful in the process of the invention can be readily prepared in high yields by the method described, for example, in Chem. Ber. 40, 642 (1907).

The process of the invention is reduced to practice using any of the reactions which have been widely utilized in the field of peptide syntheses.

The amino group of another starting compound or amino acid of the formula (II) is preferably protected prior to being subjected to a condensation reaction. Examples of the amino-protecting group include acyl groups such as an acetyl group, a propionyl group, a benzoyl group, a p-nitrobenzoyl group and the like; alkyloxycarbonyl groups such as an ethyloxycarbonyl group, a tert-butyloxycarbonyl group, a tert-amyloxycarbonyl group and the like; cycloalkyloxycarbonyl groups such as a cyclohexyloxycarbonyl group and the like; aralkyloxycarbonyl groups such as a benzyloxycarbonyl group, a p-methoxybenzyloxycarbonyl group and the like; aryloxycarbonyl groups such as an o-nitrophenoxycarbonyl group and the like; and protecting groups of the Schiff base type such as a phthaloyl group and a salicylidene group.

The condensation reaction is conducted by any of the following methods:

(1) A free N-protected amino acid of the formula (II) and 2-amino-1,3,4-thiadiazole of the formula (III) are interacted in the presence of a dehydrating agent or a condensing agent. The dehydrating agent is, for example, N,N'-dicyclohexylcarbodiimide or the like. The condensing agent is, for example, a chlorocarbonic ester or a phosphorous ester such as a dichlorphosphorous diester, a dichlorophosphorous acid monoester, tetraethyl pyrophosphate or the like.

(2) A reactive derivative of an N-protected amino acid (II) is reacted with 2-amino-1,3,4-thiadiazole (III). Examples of the reactive derivative of the N-protected amino acid include acid chlorides, azides, acid anhydrides, mixed acid anhydrides, and active esters such as a phenyl ester, a cyanomethyl ester, an N-hydroxysuccinimide ester, an N-hydroxyphthalimide ester and the like, and those generally useful in the syntheses of peptides.

(3) A free N-protected amino acid (II) is reacted with a reactive derivative of 2-amino-1,3,4-thiadiazole (III).

The reactive derivative includes, for example, an isocyanate or a phosphazo compound.

In order to carry out the condensation reaction, approximately equimolar amounts of both starting compounds (II) and (III) are reacted at temperatures ranging from $-70°$ C.$-+250°$ C. for 1-30 hours in the presence or absence of a solvent under water-free conditions, which may vary depending upon the type of each of the starting materials to be actually used. The reaction product can be isolated and purified in the usual manner known to the art.

The elimination of the amino-protecting group from the resulting condensation product is effected by conventional techniques. Favorably employed are a catalytic reduction method in which as a catalyst, use is made of palladium, platinum, Raney nickel or the like; a reduction method in which liquid ammonia is used together with either a metallic lithium or a metallic sodium; and a method in which hydrogen bromide, hydrogen chloride, hydrogen iodide or the like is reacted in a solvent such as glacial acetic acid, dioxane, nitromethane, carbon tetrachloride, diethyl phosphite, ethanol, trifluoroacetic acid or the like.

The compounds having the formula (I) of the invention include the L-, D- and DL-isomers, and particularly desirable are the L-isom in terms of their pharmaceutical effects.

The compounds of the formula (I) can be converted, in the known manner, to water-soluble acid addition salts which are pharmaceutically acceptable. Suitable acids useful in forming such addition salts include, for example, inorganic acids such as hydrochloric acid, hydrobromic acid, hydriodic acid, sulfuric acid, nitric acid, phosphoric acid and the like; and organic acids such as acetic acid, propionic acid, dichloroacetic acid, benzilic acid, salycylic acid, oxalic acid, malonic acid, adipic acid, maleic acid, fumaric acid, tartaric acid, citric acid, ascorbic acid and the like.

Typical types of compounds of the formula (I) according to the invention were tested to determine the degrees of their acute toxicity and anti-tumor efficacy with the results tabulated in Table 1.

TABLE 1

| Test Compounds (1) | Acute Toxicity (2) [$LD_{50}$ (mg/kg)] | Anti-tumor Test (3) | |
|---|---|---|---|
| | | Dose (mg/kg/day) | Survival Effect (%) |
| A | >1,600 | 400 | 154 |
| | | 200 | 141 |
| B | >500 | 400 | 161 |
| | | 200 | 144 |
| C | >500 | 400 | 157 |
| | | 200 | 116 |
| D | 357 | 200 | 157 |
| E | >1,600 | 400 | 155 |
| | | 200 | 143 |
| F | >500 | 400 | 190 |
| | | 200 | 183 |
| G | >500 | 400 | 102 |
| | | 200 | 93 |
| H | >1,600 | 400 | 124 |
| | | 200 | 121 |
| I | >1,600 | 400 | 146 |
| | | 200 | 125 |
| J | 165 | 100 | 153 |
| K | >1,600 | 600 | 119 |
| | | 460 | 116 |
| L | 1,200 | 400 | 151 |
| | | 200 | 143 |
| M | 1,200 | 400 | 156 |

TABLE 1-continued

| Test Compounds (1) | Acute Toxicity (2) [$LD_{50}$ (mg/kg)] | Anti-tumor Test (3) | |
|---|---|---|---|
| | | Dose (mg/kg/day) | Survival Effect (%) |
| | | 200 | 145 |

(1) Test Compounds
A: 2-DL-Leucylamino-1,3,4-thiadiazole.hydrochloride
B: 2-L-Leucylamino-1,3,4-thiadiazole.hydrochloride
C: 2-D-Leucylamino-1,3,4-thiadiazole.hydrochloride
D: 2-DL-Isoleucylamino-1,3,4-thiadiazole.dihydrochloride
E: 2-DL-Valylamino-1,3,4-thiadiazole.hydrochloride
F: 2-L-Valylamino-1,3,4-thiadiazole.hydrochloride
G: 2-D-Valylamino-1,3,4-thiadiazole.hydrochloride
H: 2-DL-Methionylamino-1,3,4-thiadiazole.hydrochloride
I: 2-Dl-Phenylglycylamino-1,3,4-thiadiazole.hydrobromide
J: 2-Cycloleucylamino-1,3,4-thiadiazole.hydrochloride
K: 2-L-α-Aspartylamino-1,3,4-thiadiazole.monohydrate
L: 2-L-Tryptophylamino-1,3,4-thiadiazole.hydrochloride
M: 2-L-Phenylalanylamino-1,3,4-thiadiazole.hydrobromide
(2) Acute Toxicity
The median lethal dose ($LD_{50}$) of each of the test compounds was determined by the Litchfield-Wilcoxon method after the intraperitoneal injection of the compound into ddy mice.
(3) Anti-tumor Test
Each experimental group was composed of six $CDF_1$ mice. The mice were inoculated intraperitoneally with $10^6$ P388 leukemia, and the test compounds dissolved in a physiological salt solution were administered intraperitoneally to the animals 24 hours and 5 days, respectively, after the inoculation. The survival effect of each of the compounds was expressed by the percentage of the survival days of the treated animals in each group relative to those of the control animals.

Further, the compounds of the invention possess remarkably excellent survival effects on the mice inoculated with L1210 leukemia, Ehrlich carcinoma (solid type) and Crocker sarcoma.

This invention will now be described in further detail with reference to certain specific Examples, which are presented herein for purposes of illustration only and are not to be construed as limiting unless otherwise specified.

EXAMPLE 1

(i) 9.6 g of N-benzyloxycarbonyl-DL-leucine and 3.7 g of triethylamine were dissolved in 150 ml of chloroform, to which was added dropwise 3.9 g of ethyl chlorocarbonate under sodium chloride-ice cooling conditions. The solution was stirred for 2 hours, to which was then added 3.7 g of 2-amino-1,3,4-thiadiazole, followed by stirring for further 24 hours. The reaction solution was washed with water, and after drying, the solvent was removed by distillation to obtain 9.0 g (yield: 71%) of 2-(N-benzyloxycarbonyl-DL-leucylamino)-1,3,4-thiadiazole as white crystals having a melting point of 118°–120° C.

(ii) 9.0 g of the thus obtained amino-protected product was added to a 25% hydrogen bromide-acetic acid, and the solution was reacted for 2 hours. Thereafter, ether was added to the reaction solution, and the resulting crystals were collected by filtration to obtain 7.6 g (quantitative, total yield: 71%) of 2-DL-leucylamino-1,3,4-thiadiazole. hydrobromide in the form of white crystals having a melting point of 232° C. (dec.).

(iii) 7.6 g of the hydrobromide was desalted by the usual method using an ion exchange resin (Amberlite IRA-400), thereby obtaining 5.0 g of a free base (yield: 90%, total yield: 64%) as white crystals having a melting point of 186° C. (dec.). 5.0 g of the thus obtained free base was converted to the corresponding hydrochloride using a 20% hydrogen chloride-ethanol solution and then recrystallized from ethanol to obtain 5.5 g (yield: 85% total yield: 61%) of 2-DL-leucylamino-1,3,4-thiadiazole.hydrochloride as colorless prisms having a melting point of 203° C. (dec.).

Elementary analysis:

|  | C | H | N |
|---|---|---|---|
| Calculated for $C_8H_{15}N_4ClOS$ (%) | 38.32 | 6.03 | 22.34 |
| Found (%) | 38.09 | 5.81 | 22.38 |

(iv) N-Benzyloxycarbonyl-L-leucine and N-benzyloxycarbonyl-D-leucine were treated in the same manner as in items (i), (ii) and (iii) above to obtain 2-L-leucylamino-1,3,4-thiadiazole and 2-D-leucylamino-1,3,4-thiadiazole, and acid addition salts thereof.

2-L-Leucylamino-1,3,4-thiadiazole:

Hydrobromide
mp: 213°–219° C. (dec.)
$[\alpha]_D^{20}$: +6.79° (C=2.1, EtOH)
Hydrochloride
mp: 196°–199° C. (dec.)
$[\alpha]_D^{20}$: +18.0° (C=1.1, MeOH)

2-D-Leucylamino-1,3,4-thiadiazole:

Hydrobromide
mp: 215°–219° C. (dec.)
$[\alpha]_D^{20}$: −6.25° (C=1.9, EtOH)
Free base
mp: 170°–176° C. (dec.)
$[\alpha]_D^{20}$: −1.77° (C=0.28, EtOH)
Hydrochloride
mp: 193°–199° C. (dec.)
$[\alpha]_D^{20}$: −18.5° (C=1.1, MeOH)

EXAMPLE 2

(i) 9.6 g of N-benzyloxycarbonyl-DL-isoleucine, 3.7 g of triethylamine, 150 ml of chloroform, 3.9 of ethyl chlorocarbonate and 3.7 g of 2-amino-1,3,4-thiadiazole were subjected to a reaction similar to that in Example 1(i) to obtain 10.3 g (yield: 82%) of 2-(N-benzyloxycarbonyl-DL-isoleucylamino)-1,3,4-thiadiazole as white crystals having a melting point of 145°–149° C.

(ii) 10.3 g of the thus obtained amino-protected product was reacted with a 25% hydrogen bromide-acetic acid solution in a manner similar to that in Example 1(ii) to obtain 8.7 g of 2-DL-isoleucylamino-1,3,4-thiadiazole. hydrobromide (quantitative, total yield: 81%) as white crystals having a melting point of 236° C. (dec.).

(iii) The product was desalted in a manner similar to that in Example 1(iii) to obtain 5.3 g (yield: 84%, total yield: 68%) of a free base as white crystals having a melting point of 99°–100° C. (dec.). Further, the corresponding hydrochloride was prepared in the same manner as in Example 1(iii) and recrystallized from ethanol to obtain 6.4 g (yield: 75%, total yield: 62%) of 2-DL-isoleucylamino-1,3,4-thiadiazole.dihydrochloride as colorless prisms having a melting point of 198° C. (dec.).

Elementary analysis:

|  | C | H | N | Cl |
|---|---|---|---|---|
| Calculated for $C_8H_{16}N_4Cl_2OS$ (%) | 33.45 | 5.61 | 19.51 | 24.69 |
| Found (%) | 33.76 | 5.41 | 19.79 | 24.41 |

EXAMPLE 3

(i) 26.5 g of N-benzyloxycarbonyl-DL-leucine and 10 g of 2-amino-1,3,4-thiadiazole were dissolved in 80 ml of dioxane, to which was added dropwise 20 ml of a dioxane solution of 20.6 g of N,N'-dicyclohexylcarbodiimide, followed by stirring at room temperature for 24 hours. The solvent was removed from the reaction solution by distillation under reduced pressure, and the residue was recrystallized from diluted ethanol to obtain 20.9 g (yield: 56%) of 2-(N-benzyloxycarbonyl-DL-leucylamino)-1,3,4-thiadiazole as colorless crystals having a melting point of 121° C. (dec.).

(ii) 20.9 g of the condensate obtained in item (i) above was catalytically reduced in 200 ml of ethanol in the presence of palladium chloride, and separated and purified in the usual manner to obtain 13 g (quantitative, total yield: 56%) of 2-DL-leucylamino-1,3,4-thiadiazole as colorless crystals having a melting point of 186° C. (dec.).

EXAMPLE 4

(i) 26.5 g of N-benzyloxycarbonyl-DL-isoleucine and 10 g of 2-amino-1,3,4-thiadiazole were reacted in the same manner as in Example 3(i) to obtain 19.5 g (yield: 56%) of 2-(N-benzyloxycarbonyl-DL-isoleucylamino)-1,3,4-thiadiazole as white crystals having a melting point of 149° C.

(ii) 19.5 g of the thus obtained N-protected product was reacted in the same manner as in Example 1(ii) to obtain 12.0 g (quantitative, total yield: 56%) of 2-DL-isoleucylamino-1,3,4-thiadiazole as colorless crystals having a melting point of 99°–100° C. (dec.).

EXAMPLE 5

(i) 10 g of N-benzyloxycarbonyl-DL-phenylglycine, 3.6 g of triethylamine, 150 ml of chloroform, 3.8 g of ethyl chlorocarbonate and 3.6 g of 2-amino-1,3,4-thiadiazole were reacted in the same manner as in Example 1(i) to obtain 8.2 g (yield: 63%) of 2-(N-benzyloxycarbonyl-DL-phenylglycylamino)-1,3,4-thiadiazole as white crystals having a melting point of 172°–174° C.

(ii) 8.2 g of the thus obtained amino-protected product was treated with a 25% hydrogen bromide-acetic acid solution and recrystallized from water to obtain 7.0 g (quantitative, total yield: 63% of 2-DL-phenylglycylamino-1,3,4-thiadiazole.hydrobromide as colorless prisms having a melting point of 239° C. (dec.).

Elementary analysis:

|  | C | H | N |
|---|---|---|---|
| Calculated for $C_{10}H_{11}N_4OSBr$ (%) | 38.11 | 3.52 | 17.78 |
| Found (%) | 38.40 | 3.48 | 17.97 |

(iii) The hydrobromide was desalted to obtain a free base as white crystals having a melting point of 160° C. (dec.).

EXAMPLE 6

(i) 9.5 g of N-benzyloxycarbonyl-DL-methionine, 3.4 g of triethylamine, 150 ml of chloroform, 3.7 g of ethyl chlorocarbonate and 3.4 g of 2-amino-1,3,4-thiadiazole were reacted in the same manner as in Example 1(i) to obtain 10.3 g (yield: 84%) of 2-(N-benzyloxycarbonyl-DL-methionylamino)-1,3,4-thiadiazole as white crystals having a melting point of 155°–159° C.

(ii) 10.3 g of the thus obtained amino-protected product was suspended in anisole, to which were added 7 ml of methyl ethyl sulfide and a 25% hydrogen bromide-acetic acid solution, followed by reaction at room temperature for 1 hour. The reaction solution was treated in the usual manner to obtain 8.8 g (quantitative, total yield: 84%) of 2-DL-methionylamio-1,3,4-thiadiazole.-hydrobromide as white crystals having a melting point of 207° C. (dec.).

(iii) The thus obtained hydrobromide was desalted using Amberlite IRA-400 to obtain 6.1 g (yield: 94%, total yield: 78%) of a free base as white crystals having a melting point of 150°–153° C. (dec.).

(iv) The free base was treated with a 20% hydrochloric acid-ethanol solution and recrystallized from ethanol to obtain 5.4 g (yield: 76%, total yield: 60%) of a hydrochloride as colorless flakes having a melting point of 193°–194° C. (dec.).

Elementary analysis:

|  | C | H | N |
|---|---|---|---|
| Calculated for $C_7H_{13}N_4OS_2Cl$ (%) | 31.28 | 4.87 | 20.84 |
| Found (%) | 31.68 | 4.82 | 20.96 |

EXAMPLE 7

(i) 10 g of N-benzyloxycarbonylcycloleucine, 3.9 g of triethylamine, 150 ml of chloroform, 4.1 g of ethyl chlorocarbonate and 3.9 g of 2-amino-1,3,4-thiadiazole were reacted in the same manner as in Example 1(i) to obtain 8.4 g (yield: 64%) of 2-(N-benzyloxycarbonyl-cycloleucylamino)-1,3,4-thiadiazole as white crystals having a melting point of 229°–233° C.

(ii) 8.4 g of the thus obtained amino-protected product was reacted with a 25% hydrobromic acid-acetic acid solution at room temperature for 2 hours and treated in the usual manner to obtain 7.1 g (quantitative, total yield: 64%) of 2-cycloleucylamino-1,3,4-thiadiazole.hydrobromide as white crystals having a melting point of 230° C. (dec.).

(iii) To the aqueous solution of the hydrobromide was added sodium hydroxide to render it alkaline, followed by treatment in the usual manner to obtain 4.5 g (yield: 88%, total yield: 56%) of a free base as white crystals having a melting point of 125°–127° C. (dec.).

(iv) The free base was treated with an equimolar amount of concentrated hydrochloric acid and recrystallized from ethanol to obtain 4.9 g (yield: 91%, total yield: 51%) of a hydrochloride as colorless prisms having a melting point of 199° C. (dec.).

Elementary analysis:

|  | C | H | N |
|---|---|---|---|
| Calculated for $C_8H_{13}N_4OSCl$ (%) | 38.63 | 5.27 | 22.53 |
| Found (%) | 38.48 | 5.31 | 22.14 |

EXAMPLE 8

(i) 10 g of N-benzyloxycarbonyl-DL-valine, 4.1 g of triethylamine, 150 ml of chloroform, 4.4 g of ethyl chlorocarbonate and 4.1 g of 2-amino-1,3,4-thiadiazole were reacted in the same manner as in Example 1(i) to obtain 10.5 g (yield: 79%) of 2-(N-benzyloxycarbonyl-DL-valylamino)-1,3,4-thiadiazole as white crystals having a melting point of 162°–164° C.

(ii) 10.5 g of the thus obtained amino-protected product was treated with a 25% hydrobromic acid-acetic acid solution to obtain 8.8 g (quantitative, total yield: 79%) of 2-DL-valylamino-1,3,4-thiadiazole.hydrobromide as white crystals having a melting point of 236° C. (dec.).

(iii) The hydrobromide was desalted using Amberlite IRA-400 to obtain 5.4 g (yield: 86%, total yield: 68%) of a free base as white crystals having a melting point of 104°–106° C. (dec.).

(iv) The free acid obtained in item (iii) above was treated with an equimolar amount of concentrated hydrochloric acid and recrystallized from ethanol to obtain 5.9 g (yield: 93%, total yield: 63%) of a hydrochloride as colorless prisms having a melting point of 218° C. (dec.).

Elementary analysis:

|  | C | H | N |
|---|---|---|---|
| Calculated for $C_7H_{13}N_4OSCl$ (%) | 35.52 | 5.54 | 23.67 |
| Found (%) | 35.79 | 5.46 | 23.53 |

(v) N-Benzyloxycarbonyl-L-valine and N-benzyloxycarbonyl-D-valine were treated in the same manner as in items (i) to (iv) above to obtain 2-L-valylamino-1,3,4-thiadiazole and 2-D-valylamino-1,3,4-thiadiazole, and acid addition salts thereof.

2-L-Valylamino-1,3,4-thiadiazole:

Hydrobromide
mp: 229°–230° C. (dec.)
$[\alpha]_D^{20}$: +21.6° (C=1.3, MeOH)
Free base
mp: 125°–126° C. (dec.)
$[\alpha]_D^{20}$: +16.5° (C=1.3, MeOH)
Hydrochloride
mp: 203°–204° C. (dec.)
$[\alpha]_D^{20}$: +35.0° (C=1.0, MeOH)

2-D-Valylamino-1,3,4-thiadiazole:

Hydrobromide
mp: 222°–227° C. (dec.)
$[\alpha]_D^{20}$: −19.7° (C=1.4, MeOH)
Free base
mp: 126°–128° C. (dec.)
$[\alpha]_D^{20}$: −4.55° (C=1.1, MeOH)
Hydrochloride
mp: 199°–200° C. (dec.)
$[\alpha]_D^{20}$: −35.5° (C=1.1, MeOH)

EXAMPLE 9

(i) Using the same procedure as in Example 1(i), 10 g of a β-benzyl ester of N-t-butoxycarbonyl-L-aspartic acid, 3.1 g of triethylamine, 3.4 g of ethyl chlorocarbonate and 3.1 g of 2-amino-1,3,4-thiadiazole were reacted in 100 ml of chloroform to obtain 8.1 g (yield: 64%) of a β-benzyl ester of 2-(N-t-butoxycarbonyl-L-α-aspartylamino)-1,3,4-thiadiazole as white crystals of mp: 112°–114° C. and $[\alpha]_D^{20}$: −30.0° (C=1.0, MeOH).

(ii) 8.1 g of the resulting condensation product was treated with an alkali at room temperature for 1 hour to obtain 5.9 g (yield: 93%) of 2-(N-t-butoxycarbonyl-L-α-aspartylamino)-1,3,4-thiadiazole as white powder of mp: 120°–128° C. (dec.) and $[\alpha]_D^{20}$: −40.8° (C=1.1, MeOH).

(iii) 5.9 g of the thus obtained amino-protected product was treated with a dioxane solution of hydrogen chloride at room temperature for 2 hours to remove the amino-protecting group. A crude hydrochloride of mp: 150°–154° C. (dec.) and $[\alpha]_D^{20}$: +7.4° (C=1.0, MeOH) was obtained (quantitative yield: 4.7 g). The resulting hydrochloride in the amount of 4.7 was dissolved in water and neutralized with an alkali, and the free base was recrystallized from water to obtain 2.9 g (yield: 66%) of 2-L-α-aspartylamino-1,3,4-thiadiazole.-monohydrate as colorless prisms of mp: 151° C. (dec.) and $[\alpha]_D^{20}$: +31.1° (C=1.0, H$_2$O).

Elementary analysis:

|  | C | H | N |
|---|---|---|---|
| Calculated for C$_6$H$_{10}$N$_4$O$_4$S (%) | 30.77 | 4.30 | 23.92 |
| Found (%) | 30.38 | 4.14 | 23.66 |

EXAMPLE 10

(i) Using the same procedure as in Example 1(i), 10 g of N-t-butoxycarbonyl-DL-threonine, 4.6 g of triethylamine, 5.0 g of ethyl chlorocarbonate and 4.6 g of 2-amino-1,3,4-thiadiazole were reacted in 150 ml of tetrahydrofuran to obtain 10.9 g (yield: 79%) of 2-(N-t-butoxycarbonyl-DL-threonylamino)-1,3,4-thiadiazole as white powder having a melting point of 165°–170° C. (dec.).

(ii) 10.9 g of the thus obtained amino-protected product was treated with a dioxane solution of hydrogen chloride at room temperature for 2 hours to remove the amino-protecting group. The resulting hydrochloride was recrystallized from methanol to obtain 7.5 g (yield: 87%) of 2-DL-threonylamino-1,3,4-thiadiazole.hydrochloride as colorless prisms having a melting point of 218° C. (dec.).

Elementary analysis:

|  | C | H | N |
|---|---|---|---|
| Calculated for C$_6$H$_{11}$N$_4$O$_2$SCl (%) | 30.19 | 4.64 | 23.47 |
| Found (%) | 30.05 | 4.67 | 23.63 |

EXAMPLE 11

(i) Using the same procedure as in Example 1(i), 10 g of N-t-butoxycarbonyl-L-tryptophan, 3.3 g of triethylamine, 3.5 g of ethyl chlorocarbonate and 3.3 g of 2-amino-1,3,4-thiadiazole were reacted in 150 ml of chloroform to obtain 10.7 g (yield: 84%) of 2-(N-t-butoxycarbonyl-L-tryptophanylamino)-1,3,4-thiadiazole as light yellow powder of mp: 98°–101° C. (dec.) and $[\alpha]_D^{20}$: +41.0° (C=1.0, MeOH).

(ii) 10.7 g of the thus obtained amino-protected product was treated with a hydrogen chloride-dioxane solution and then with 2-mercaptoethanol at room temperature for 2 hours to remove the amino-protecting group. The resulting hydrochloride was recrystallized from methanol to obtain 7.3 g (yield: 82%) of 2-L-tryptophanylamino-1,3,4-thiadiazole.hydrochloride as pinky prisms of mp: 210° C. (dec.) and $[\alpha]_D^{20}$: +93.0° (C=1.0, MeOH).

Elementary analysis:

|  | C | H | N |
|---|---|---|---|
| Calculated for C$_{13}$H$_{14}$N$_5$OSCl (%) | 48.22 | 4.36 | 21.63 |
| Found (%) | 48.34 | 4.28 | 21.70 |

EXAMPLE 12

(i) Using the same procedure as in Example 1(i), 10 g of N-benzyloxycarbonyl-L-phenylalanine, 3.3 g of triethylamine, 3.7 g of ethyl chlorocarbonate and 3.5 g of 2-amino-1,3,4-thiadiazole were reacted in chloroform to obtain 9.1 g (yield: 71%) of 2-(N-benzyloxycarbonyl-L-phenylalanylamino)-1,3,4-thiadiazole as white crystals of mp: 78°–83° C. and $[\alpha]_D^{20}$: +28.0° (C=1.2, MeOH).

(ii) 9.1 g of the thus obtained amino-protected product was treated with a 25% hydrogen bromide-acetic acid solution and recrystallized from methanol to obtain 6.2 g (yield: 79%) of 2-L-phenylalanylamino-1,3,4-thiadiazole.hydrobromide as colorless prisms of mp: 231° C. (dec.) and $[\alpha]_D^{20}$: +55.1° (C=1.4, MeOH).

(iii) 2-L-Phenylalanylamino-1,3,4-thiadiazole.hydrochloride:

colorless prisms
mp: 205°–206° C. (dec.)
$[\alpha]_D^{20}$: +86.1° (C=1.0, MeOH)

(iv) 2-L-Phenylalanylamino-1,3,4-thiadiazole:
white powder
mp: 133° C. (dec.)
$[\alpha]_D^{20}$: +35.2° (C=1.2, MeOH)

Having fully described the invention, it will be apparent to one skilled in this art that many changes and modifications can be made without departing from the spirit or scope of the appended claims.

What is claimed as new and intended to be covered by Letters Patent is:

1. A compound represented by the formula, $$R_2-\underset{\underset{NH_2}{|}}{\overset{\overset{R_1}{|}}{C}}-CONH-\underset{S}{\overset{N-\!-\!-\!N}{\parallel\quad\parallel}}$$

wherein R$_1$ represents a hydrogen atom, and R$_2$ represents a lower alkyl group, a phenyl group, a benzyl group, a lower alkylthio lower alkyl group, a lower alkyl group substituted by a carboxyl or hydroxyl group, or a 3-indolylmethyl group, or wherein R$_1$ and R$_2$ define in combination a C$_4$-alkylene group, or a pharmaceutically acceptable acid addition salt thereof.

2. The compound of claim 1, wherein said pharmaceutically acceptable acid addition salt is in the form of a hydrochloride or a hydrobromide.

3. The compound of claim 1, which is in the form of an L-isomer, a D-isomer or a DL-isomer.

* * * * *